US008813746B2

(12) United States Patent
Mansour

(10) Patent No.: US 8,813,746 B2
(45) Date of Patent: Aug. 26, 2014

(54) NASAL CONTINUOUS POSITIVE AIRWAY PRESSURE DEVICE FOR LOWERING PATIENT WORK-OF-BREATHING

(75) Inventor: Khalid Mansour, Yorba Linda, CA (US)

(73) Assignee: Carefusion 303, Inc., San Diego, CA (US)

( * ) Notice: Subject to any disclaimer, the term of this patent is extended or adjusted under 35 U.S.C. 154(b) by 876 days.

(21) Appl. No.: 12/880,041

(22) Filed: Sep. 10, 2010

(65) Prior Publication Data

US 2012/0060844 A1 Mar. 15, 2012

(51) Int. Cl.
*A62B 9/00* (2006.01)
*A62B 7/00* (2006.01)
*A61M 16/00* (2006.01)

(52) U.S. Cl.
USPC ............ 128/204.24; 128/204.18; 128/204.25; 128/207.18

(58) Field of Classification Search
USPC .............. 128/204.18, 207.18, 204.24, 204.25
See application file for complete search history.

(56) References Cited

U.S. PATENT DOCUMENTS

| 5,193,532 | A  | 3/1993 | Moa et al. |
| 7,578,294 | B2 | 8/2009 | Pierro et al. |
| 2007/0074724 | A1 | 4/2007 | Duquette et al. |
| 2009/0165799 | A1 | 7/2009 | Duquette et al. |

OTHER PUBLICATIONS

International Search Report and Written Opinion for PCT/US2011/047965 mailed Mar. 26, 2012.

*Primary Examiner* — Justine Yu
*Assistant Examiner* — Michael Tsai
(74) *Attorney, Agent, or Firm* — McDermott Will & Emery LLP

(57) ABSTRACT

A nasal continuous positive airway pressure device for lowering patient work-of-breathing is described. The device may include an inspiratory tubing in fluid communication with at least two nasal prongs; expiratory tubing; and a generator body coupled therebetween. The generator body may include at least two jets configured for receiving gas from the inspiratory tubing; and a flow enhancer configured for directing received gas. The flow enhancer may include a gas manager configured for channeling received gas towards a jet impingement point via at least two jet paths; a fluidic flip trigger configured for triggering a fluidic flip of channeled gas back towards the expiratory tubing by directing a first portion of exhaled patient breath towards the jet impingement point along a first pathway; and an isolated pathway manager configured for directing a second portion of the exhaled patient breath along a second pathway towards the expiratory tubing.

19 Claims, 3 Drawing Sheets

NASAL CONTINUOUS POSITIVE AIRWAY PRESSURE DEVICE FOR LOWERING PATIENT WORK-OF-BREATHING

FIELD OF THE INVENTION

The present technology relates generally to the respiratory field. More particularly, the present technology relates to a variable flow nasal continuous positive airway pressure device.

BACKGROUND

In general, continuous positive airway pressure (CPAP) is a method of respiratory ventilation used primarily to treat patients experiencing respiratory difficulties and/or insufficiencies. For example, CPAP is used for critically ill patients in a hospital with respiratory failure. In these patients, PAP ventilation can prevent the need for tracheal intubation, or allow earlier extubation. Sometimes patients with neuromuscular diseases use this variety of ventilation as well.

With infants, however, a less invasive patient interface device is desirable. In particular, one that interfaces directly or indirectly with the nasal airways via the patient's nares, such as a mask or nasal prongs, is generally used. Such systems are commonly referred to as nasal continuous positive airway pressure (nCPAP) systems.

DESCRIPTION OF EMBODIMENTS

Figure 1:
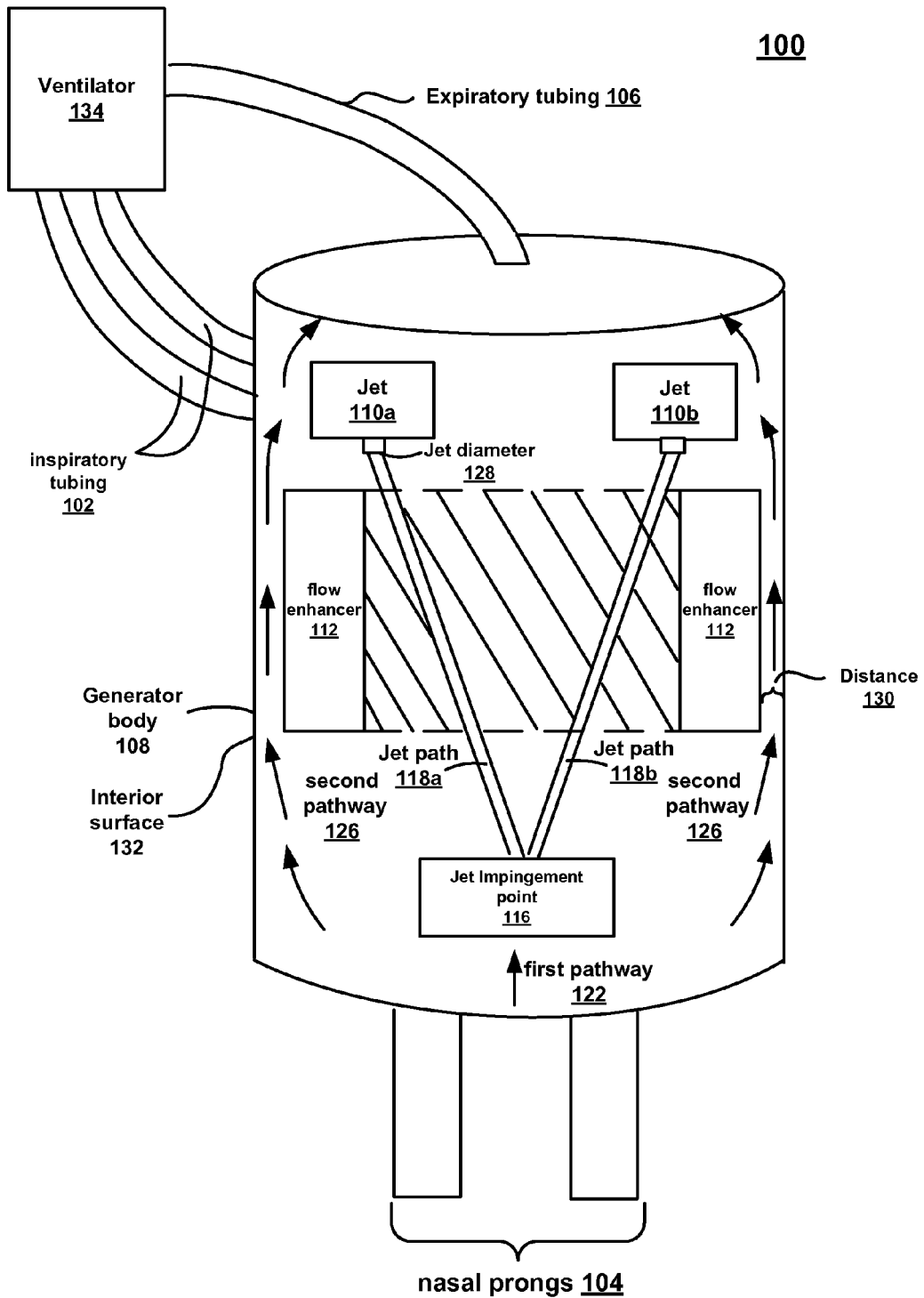
FIG. 1 is a perspective view of a nasal continuous positive airway pressure device for lowering patient work-of-breathing, according to one embodiment of the present technology.

The drawings referred to in this description should not be understood as being drawn to scale unless specifically noted.

DESCRIPTION OF EMBODIMENTS

The discussion will begin with an overview of the general use of nasal continuous positive airway pressure devices and the limitations associated therewith. The discussion will then focus on embodiments of the present technology that provide a nasal continuous positive airway pressure device for lowering patient work of breathing.

OVERVIEW

In general, nasal continuous positive airway pressure (nCPAP) devices assist infants with under-developed lungs by preventing lung collapse during exhalation and assisting in lung expansion during inhalation. One type of interface device that couples the generator body of a nCPAP with the infant are nasal prongs.

With ventilator-based CPAP devices, a relative constant and continuous flow of gas (e.g., air, O2, etc.) is delivered into the patient's airways. This airflow creates a pressure within a patient's lungs via a restriction placed on outflow from the patient. However, the patient is required to exhale against the incoming gas, which increases the patient's work of breathing (WOB).

Embodiments of the present technology provide a nasal continuous positive airway pressure (nCPAP) device for lowering a patient's WOB. Firstly, in one embodiment, the flow enhancer of the nCPAP device redirects a jet flow of gas that was originally directed towards a patient's nares to a jet impingement point. Channeling the dual jet flows into a common jet flow that is moving toward the patient's nares enables the patient to more easily inhale the oxygen, and thus decreases WOB.

Secondly, in one embodiment, the flow enhancer of the nCPAP device directs a first portion of the exhaled patient breath towards the channeled jet flow directed at the jet impingement point. Directing the exhaled breath to meet this channeled jet flow head on causes, through a "fluidic flip" effect, the channeled jet flow (airstream) directed towards the patient's nares to reverse direction. Thus, both the channeled jet flow now traveling in the reverse direction and the exhaled patient breath now flow to the expiratory tubing. Thus, by causing the jetstream directed towards the patient's nares to reverse direction during the patient's exhalation, the patient does not have to expend lung energy exhaling into an continuously incoming stream of air. Consequently, reversing the direction of the jetstream during the first part of the patient's exhalation lowers the patient's WOB.

Thirdly, in one embodiment, the flow enhancer of the nCPAP device directs a second portion of the exhaled patient breath along a pathway, separate and isolated from the pathway caused by the "fluidic flip" effect, towards the expiratory tubing. This second portion does not encounter resistance as it flows to the expiratory tubing. Consequently, since the patient does not have to breath the second portion of exhaled air into any incoming airstream, the resistance to exhaled patient breath is lowered, thus lowering the patient's WOB.

Therefore, embodiments of the present technology provide for a method of lowering the patient's WOB by increasing an airflow to the patient during patient inhalation as well as reducing resistances to the patient's exhalation.

The following discussion will begin with a description of the structure of the components of the present technology. This discussion will then be followed by a description of the components in operation.

Structure

Figure 2:
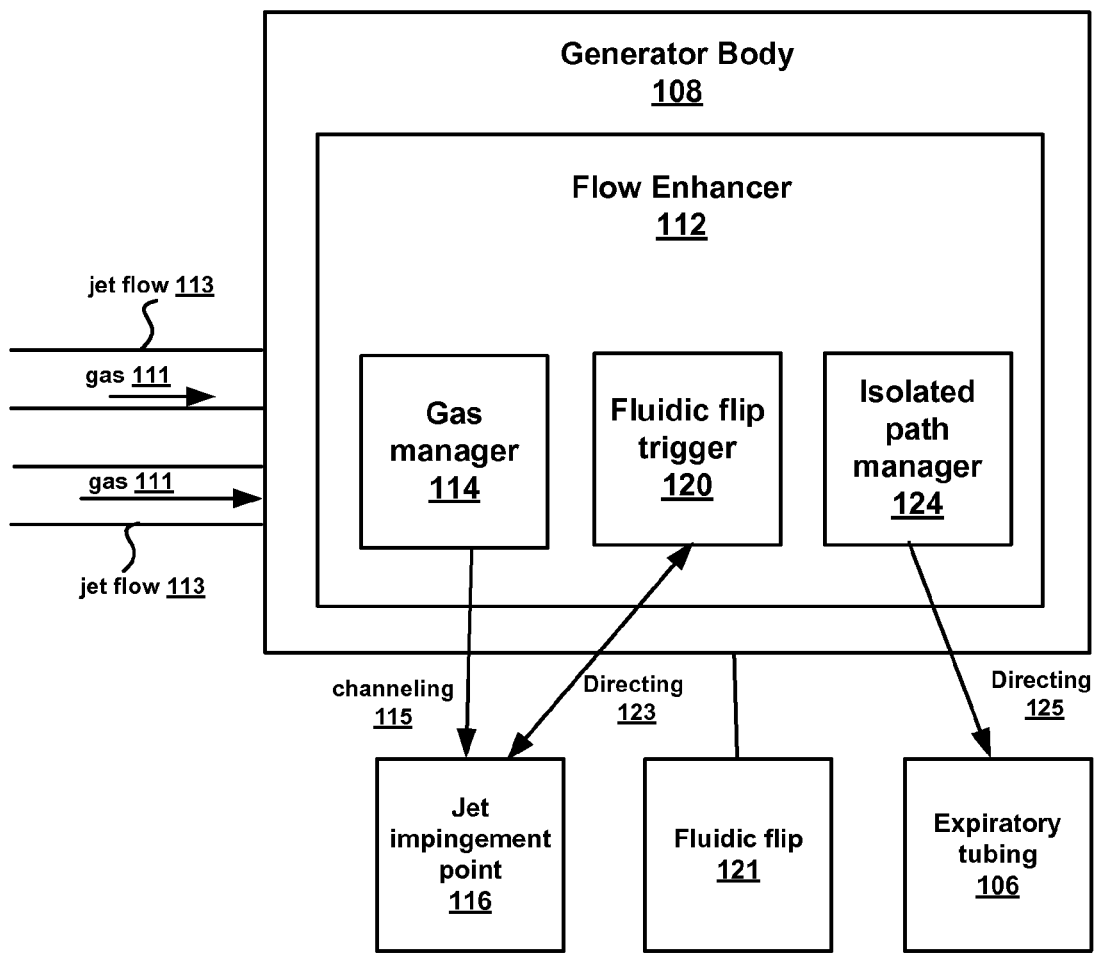
FIG. 2 is a perspective view of a flow enhancer of a generator body of a nasal continuous positive airway pressure device for lowering patient work-of-breathing, according to one embodiment of the present technology.

FIG. 1 is a perspective view of a nasal continuous positive airway pressure (nCPAP) device for lowering patient WOB, in accordance with embodiments of the present technology. FIG. 2 is a perspective view of a flow enhancer of a generator body of a nCPAP device for lowering patient WOB, in accordance with one embodiment of the present technology.

With reference now to FIGS. 1 and 2, in one embodiment, the nCPAP device 100 includes inspiratory tubing 102 in fluid communication with at least two nasal prongs 104, expiratory tubing 106, and a generator body 108 coupled with the inspiratory and expiratory tubing, 102 and 106, respectively. In one embodiment, the inspiratory tubing 102 is coupled with a ventilator 134. In another embodiment, the at least two nasal prongs 104 are positioned within nare of a patient. It should be appreciated that the term "inspiratory tubing" may refer to an "inspiratory limb", as is also used herein.

The generator body 108 includes at least two jets 110a and 110b and a flow enhancer 112. In one embodiment, the at least two jets 110a and 110b are configured for receiving gas 111 from the inspiratory tubing 102 and directing, via a jet flow 113, the gas 111 towards the at least two nasal prongs 104. In one embodiment, the at least two jets 110a and 110b have a jet diameter 128 greater than 0.034 in. In one embodiment, the jet diameter 128 is 0.044 in. It should be appreciated that the larger the jet diameter 128, the slower the jet flow 113. In one embodiment, the at least two jet paths 118*a* and 118*b* are situated angularly with respect to each other. In other words, the jet paths 118*a* and 118*b*, are not parallel with each other.

In another embodiment, the flow enhancer 112 is configured for redirecting the gas 111 of the jet flow 113. In one embodiment, the flow enhancer 112 is spaced a distance apart from an interior surface 132 of the generator body 108 to accommodate the second pathway 126. While it is shown in FIG. 1 that the expiratory tubing 106 is on top of the generator body 108, it should be appreciated that the expiratory tubing may be coupled with other areas of the generator body 108. For example, the expiratory tubing 106 may be coupled with the generator body 108 next to the flow enhancer 112. In this case, the exhaled patient's breath traveling along second pathway 126, exits the expiratory tubing 106 while next to the flow enhancer 112.

In one embodiment, the flow enhancer 112 circles around the interior surface 132 of the generator body 108. In one embodiment, the length of the flow enhancer 112 as viewed form FIG. 1, may vary. In one embodiment, the thickness of the flow enhancer 112 may be any thickness that is compatible with the nCPAP device that functions to lower the patient's WOB.

In one embodiment, the flow enhancer 112 is positioned in parallel with a nare path of a patient. The nare path of the patient is also parallel with the nasal prongs 104 of the nCPAP device 100 since the nasal prongs 104 are inserted into the patient's nares for functioning.

Referring still to FIGS. 1 and 2, in one embodiment, the flow enhancer 112 includes at least one of the following: a gas manager 114; a fluidic flip trigger 120 and an isolated pathway manager 124. In one embodiment, the gas manager 114 is configured for channeling 115 the jet flow 113 towards a jet impingement point 116 via at least two jet paths 118*a* and 118*b*.

In one embodiment, the fluidic flip trigger 120 is configured for triggering a fluidic flip 121 of channeled gas back towards the expiratory tubing 106. The fluidic flip 121 is triggered by directing 123 a first portion of the exhaled patient breath towards the jet impingement point 116 along a first pathway 122.

In another embodiment, the isolated pathway manager 124 is configured for directing 125 a second portion of the exhaled patient breath along a second pathway 126 towards the expiratory tubing 106, the second pathway 126 isolated from the first pathway 122.

Thus, embodiments of the present technology provide for a nCPAP device for lowering a patient's WOB. This is accomplished by reducing resistances throughout the generator body 108 to patient's inhalation and exhalation.

Operation

Figure 3:
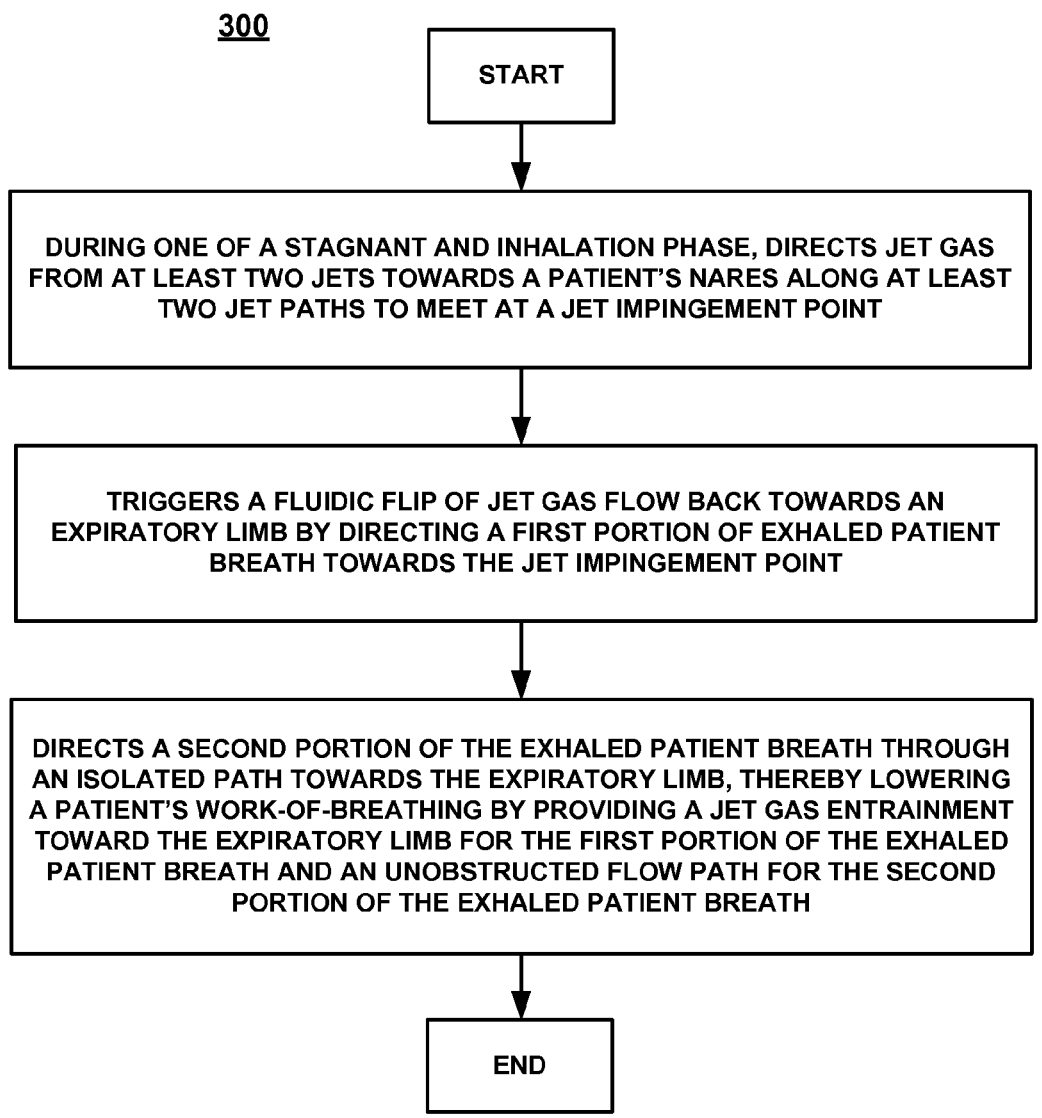
FIG. 3 is a flow diagram of a method for delivering a nasal continuous positive airway pressure to a patient, according to one embodiment of the present technology.

FIG. 3 is a flow diagram of a method 300 for delivering a nasal continuous positive airway pressure to a patient, according to one embodiment of the present technology. Referring to FIG. 3, at 302, in one embodiment and as described herein, during one of a stagnant and inhalation phase, jet gas 111 is directed from at least two jets 110*a* and 110*b* towards a patient's nares along at least two jet paths 118*a* and 118*b* to meet at a jet impingement point 116.

In one embodiment and as described herein, at 304 of FIG. 3, a fluidic flip 121 of jet gas flow back towards an expiratory limb 106 is triggered by directing 123 a first portion of exhaled patient breath towards the jet impingement point 116.

In one embodiment and as described herein, at 306 of FIG. 3, a second portion of the exhaled patient breath is directed 125 through an isolated path towards the expiratory limb 106. The foregoing method 300 lowers a patient's WOB by providing a jet gas entrainment toward the expiratory limb 106 for the first portion of the exhaled patient breath and an unobstructed flow path for the second portion of the exhaled patient breath.

All statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A nasal continuous positive airway pressure (nCPAP) device for lowering patient work-of-breathing, said nCPAP device comprising:
   inspiratory tubing in fluid communication with at least two nasal prongs;
   expiratory tubing; and
   a generator body coupled with said inspiratory tubing and said expiratory tubing, said generator body comprising:
   at least two jets configured for receiving gas from said inspiratory tubing and directing, via a jet flow, said gas towards said at least two nasal prongs; and
   a flow enhancer configured for redirecting said jet flow, said flow enhancer comprising:
   a gas manager configured for channeling said jet flow towards a jet impingement point via at least two jet paths;
   a fluidic flip trigger configured for triggering a fluidic flip of channeled gas back towards said expiratory tubing by directing a first portion of exhaled patient breath towards said jet impingement point along a first pathway; and
   an isolated pathway manager configured for directing a second portion of said exhaled patient breath along a second pathway extending around an outer wall of said flow enhancer within said generator body to said expiratory tubing, said second pathway isolated from said first pathway.

2. The nCPAP of claim 1, wherein said at least two jets have a jet diameter greater than 0.034 in.

3. The nCPAP of claim 1, wherein said flow enhancer is spaced a distance apart from an interior surface of said generator body to accommodate said second pathway.

4. The nCPAP of claim 3, wherein said flow enhancer circles around said interior surface of said generator body.

5. The nCPAP of claim 1, wherein said flow enhancer is configured to be positioned in parallel with a nare path of a patient.

6. The nCPAP of claim 1, wherein said at least two jet gas paths are situated angularly with respect to each other.

7. The nCPAP of claim 1, wherein said inspiratory tubing is coupled with a ventilator.

8. The nCPAP of claim 1, wherein said at least two nasal prongs are configured to be positioned within nare of a patient.

9. A method for delivering a nasal continuous positive airway pressure to a patient, said method comprising:
   during one of a stagnant and inhalation phase, directing jet gas from at least two jets towards a patient's nares along at least two jet paths to meet at a jet impingement point;

triggering a fluidic flip of jet gas flow back through a flow enhancer towards an expiratory limb by directing a first portion of exhaled patient breath towards said jet impingement point; and directing a second portion of said exhaled patient breath through an isolated path towards said expiratory limb, thereby lowering a patient's work-of-breathing by providing a jet gas entrainment toward said expiratory limb for said first portion of said exhaled patient breath and an unobstructed flow path for said second portion of said exhaled patient breath, wherein said unobstructed flow path for said second portion extends around an outer wall of said flow enhancer within a generator body to said expiratory limb said unobstructed flow path isolated from said isolated pathway.

10. A flow enhancer disposed within a generator body for use in a nasal continuous positive airway pressure (nCPAP) device for lowering patient work-of-breathing, said flow enhancer comprising:

a gas manager configured for redirecting a jet flow of gas towards a jet impingement point via at least two jet paths;

a fluidic flip trigger configured for triggering a fluidic flip of redirected gas back towards a expiratory limb by directing a first portion of exhaled patient breath towards said jet impingement point along a first pathway; and an isolated pathway manager configured for directing a second portion of said exhaled patient breath through a second pathway extending around an outer wall of said flow enhancer within said generator body to said expiratory limb, said second pathway isolated from said first pathway.

11. The nCPAP of claim 10, wherein said flow enhancer is spaced a distance apart from an interior surface of said generator body to accommodate said second pathway.

12. The nCPAP of claim 11, wherein said flow enhancer circles around said interior surface of said generator body.

13. The nCPAP of claim 10, wherein said flow enhancer is configured to be positioned in parallel with a nare path of a patient.

14. The nCPAP of claim 10, wherein said at least two jet gas paths are situated angularly with respect to each other.

15. A nasal continuous positive airway pressure (nCPAP) device for use in an nCPAP system for lowering patient work-of-breathing, said nCPAP device comprising:

at least two inspiratory limbs coupled with a ventilator and in fluid communication with a pair of nasal prongs;

a generator body coupled with said at least two inspiratory limbs and configured for conveying gas received from said at least two inspiratory limbs to said pair of nasal prongs, said generator body comprising:

a flow enhancer configured for redirecting gas moving within said generator body to a pathway of lesser resistance including a first pathway and a second pathway, thereby lowering said patient work-of-breathing;

an expiratory limb coupled with said generator body, said expiratory limb configured for receiving and expelling exhaled patient breath, wherein said second pathway extends around an outer wall of said flow enhancer within said generator body to said expiratory limb; and an isolated pathway manager configured for directing a second portion of said exhaled patient breath through said second pathway, said second pathway isolated from said first pathway.

16. The nCPAP device of claim 15, wherein said flow enhancer comprises:

a gas manager configured for channeling gas moving within said generator body towards a jet impingement point via at least two jet paths.

17. The nCPAP device of claim 16, wherein said flow enhancer further comprises:

a fluidic flip trigger configured for triggering a fluidic flip of channeled gas back towards said expiratory limb by directing a first portion of exhaled patient breath towards said jet impingement point along said first pathway.

18. The nCPAP of claim 15, wherein said flow enhancer is spaced a distance apart from an interior surface of said generator body to accommodate said second pathway.

19. The nCPAP of claim 18, wherein said flow enhancer circles around said interior surface of said generator body.

* * * * *